United States Patent [19]

Albrecht et al.

[11] Patent Number: 5,026,544
[45] Date of Patent: Jun. 25, 1991

[54] METHODS AND COMPOSITIONS FOR INHIBITING THE GROWTH OF NEOPLASTIC CELLS

[75] Inventors: Thomas B. Albrecht; Thomas E. Albrecht; William R. Fleischmann, all of Galveston, Tex.

[73] Assignee: Board of Reagents, The University of Texas System, Austin, Tex.

[21] Appl. No.: 156,704

[22] Filed: Feb. 16, 1988

[51] Int. Cl.[5] .................... A61K 31/485; A61K 37/66
[52] U.S. Cl. .................................. 424/85.4; 514/307; 514/2; 424/85.5; 424/85.6; 424/85.7
[58] Field of Search ..................... 424/85, 85.4, 85.5, 424/85.6, 85.7; 530/351; 514/307, 2

[56] References Cited

U.S. PATENT DOCUMENTS 4,018,927 4/1977 Voorhees ........................... 424/260
4,800,081 1/1989 Albrecht et al. ................... 424/129

OTHER PUBLICATIONS

Interferon: An Anti-Cancer Agent? Priestman, Cancer Treatment Reviews (1979), 6,223-237.
Does Interferon Cure Cancer? Sikora, British Medical Journal 281,855 (1980).
Coburn et al. (1979), Neoplastic Transformation in Differentiated Epithelial Cell Systems., In Vitro, eds. Franks & Wigley, Acad. Press, N.Y., pp. 113-114.

Primary Examiner—Richard A. Schwartz
Assistant Examiner—S. Nolan
Attorney, Agent, or Firm—Arnold, White & Durkee

[57] ABSTRACT

The present disclosure is directed to the use of combinations of a papaverine family member agent together with an interferon for the treatment of proliferative disorders such as neoplasias and hyperplasias. Disclosed are compositions and formulations which take advantage of the synergistic antiproliferative activities of these agents and the use of these compositions and formulations in the treatment of these disorders.

14 Claims, 1 Drawing Sheet

METHODS AND COMPOSITIONS FOR INHIBITING THE GROWTH OF NEOPLASTIC CELLS

The government may own certain rights in the present invention pursuant to NIH Grants AI42557 and CA76475.

BACKGROUND OF THE INVENTION

Reference is hereby made to co-pending Ser. No. 06/916,008, filed Oct. 6, 1986, now allowed; Ser. No. 06/871,120, filed June 5, 1986, now U.S. Pat. No. 4,800,031; Ser. No. 06/944,301, filed Dec. 19, 1986, now U.S. Pat. No. 4,849,412; Ser. No. 07/002,981, filed Jan. 13, 1987, now U.S. Pat. No. 4,782,065. The disclosures of the foregoing are also herein incorporated by reference.

1. Field of the Invention

The present invention relates to novel methods for the treatment of neoplastic conditions through administration of calcium flux blockers of the papaverine family in combination with one or more of the interferons. The present invention also relates to pharmaceutical compositions which include the combination of an effective concentration of a papaverine family agent in combination with one or more of the interferons.

2. Description of the Related Art

Neoplastic and hyperplastic disorders constitute a major health problem in the world today, with relatively few antineoplastic agents having the desirable properties of both efficacy and reduced toxicity. In fact, the vast majority of antitumor agents currently in use are generally both relatively non-tumor specific, as well as highly toxic to the patient being treated. For example, typical toxicities associated with antitumor therapy include depression or even destruction of bone marrow, gastro intestinal tract cells, or any of a host of other "normal" cells having higher than average growth rates.

Biological compounds such as cytokines, lymphokines and the like have been identified which exhibit some degree of antitumor or antiproliferative actions. These biological compounds tend to offer the advantage of a somewhat reduced overall toxicity and, in general, most biological anticellular agents are fairly well tolerated at therapeutically employed dose levels. For example, the principle side affects associated with interferon therapy, whether it be therapy using alpha, beta, gamma interferon, or a mixture of these, are the so-called "constitutional" symptoms of fever, chill, myalgias, headaches, malaise and the like. Moreover, agents such as tumor necrosis factor (TNF), lymphotoxin and related cytokines tend to exhibit similar side effects. This is not to mean that all biologicals are free of toxicity problems. For example, a fairly significant toxicity has been ascribed to biologicals such as interleukin-2 (IL-2) which are employed to activate killer cells, e.g., by adoptive immunotherapy.

Unfortunately, while biologicals such as the interferons tend to exhibit generally acceptable toxicity levels, they often tend to be hampered by an overall low antiproliferative potency. Moreover, while agents such as the interferons, for example, tend to exhibit relatively mild side effects on the whole, these side effects are, nevertheless, often both dose-dependent and dose-limiting. Thus, there is a practical limit to how much drug can be administered in order to achieve a desired antiproliferative affect. Accordingly, there is currently a great need for methods or other agents which can be employed to improve the potency of biologicals such as interferon without, of course, introducing any of their own additional toxicities.

In U.S. Pat. No. 4,663,317, as well as the co-pending applications listed above, it is demonstrated that certain classes of smooth muscle relaxing agents tend to exhibit profound, clinically significant antiviral activity. These smooth muscle relaxing agents are characterized functionally in terms of their action as calcium influx blockers, intracellular calcium flux inhibitors and/or cyclic nucleotide modulators. Moreover, it has been found that agents from one of the foregoing groups tend to exhibit synergistic activity when employed in combination with agents from another of the foregoing groups.

Probably the most significant single antiviral agent of the foregoing smooth muscle relaxers is papaverine and its various antivirally active congeners defined as those papaverine family agents having an intact isoquinoline ring structure, for example, as described in Ser. No. 06/944,301. These papaverine family members (isoquinoline ring congeners) tend to exhibit truly surprising antiviral activity, particularly in the treatment of human cytomegalovirus (HCMV) infections. However, there is no suggestion from these or any related disclosures known to the present inventors which would tend to suggest the usefulness of the papaverine family agents in combination with the interferons, whether alpha, beta, gamma or mixtures thereof, in the treatment of neoplastic or hyperplastic conditions or disorders.

However, it has now been discovered that not only are the papaverine agents useful as antivirals, but unexpectedly, they have proven to function synergistically with interferons to dramatically enhance the antiproliferative, as well as the antiviral, actions of the interferons.

SUMMARY OF THE INVENTION

Accordingly, it is an object of the present invention to address at least some of the deficiencies in the art by providing a class of agents which may be employed to dramatically enhance the antiproliferative activity of the interferons.

It is a more particular object of the present invention to provide agents which act synergistically with interferons to enhance their antiproliferative activity without increasing their toxicities.

It is a still further object of the present invention to provide useful compositions which include relatively non-toxic antiproliferative agents, which may, for example, be employed in the treatment of various proliferative disorders including cancers such as sarcomas, carcinomas and leukemias.

In accordance with these objects, a method is provided for the treatment of human proliferative diseases such as cancers, and in particular, leukemias, through the use of a combination of agents heretofore unknown to possess synergistic antiproliferative activity. These agents can be classified in a broad sense as the combination of a papaverine family agent, defined as a papaverine agent having an intact isoquinoline ring structure, in combination with an interferon, including interferon alpha, beta and/or gamma.

The invention is, therefore, directed to a method for inhibiting the proliferation of neoplastic or hyperplastic cells comprising subjecting such cells to an effective concentration of a papaverine family agent in combination with an interferon. Useful papaverine family agents include drugs such as papaverine, ethaverine and dioxyline.

In general, it has been discovered that the interferons as a group tend to be synergistically activated when employed in combination with a papaverine family agent. Thus, for example, the invention is directed to the combination and use of a papaverine family agent together with interferon alpha, beta, gamma or combinations of these. However, most preferably, the papaverine family agent employed is papaverine itself and the interferon most preferred is interferon gamma.

In terms of spectrum of activity, it is proposed that the usefulness of the present invention will be coextensive with that of the interferon itself. That is, in those situations where interferon is typically indicated for its antiproliferative actions, the present invention will provide a distinct benefit. These conditions include a fairly wide spectrum of antitumor and antiproliferative actions, including, for example, the use of interferon gamma in the treatment of sarcomas, carcinomas and leukemias. Moreover, in the case of interferon alpha and/or beta, one will typically find utility in the treatment of a wide spectrum of tumors and the like, for example, sarcomas and carcinomas. For a review of the interferons and their spectrum of activity, please see Baron, et al., *The Interferon System: A Review to 1987*, Austin, The University of Texas Press, 1987, and Bonnem and Spiegel, (1984), *J. Biol. Resp. Modifiers*, 3:580–598 (incorporated herein by reference).

In terms of effective doses, it should be appreciated that the dose of interferon preferably employed is that dose typically recommended in the treatment of the respective neoplastic disorder. Thus, interferon alpha and/or beta will be employed at levels on the order of $1 \times 10^5$ to $5 \times 10^8$ units/dose, or more preferably on the order of $10^7$ to $10^8$ units/dose Moreover, in the case of interferon gamma, one will also preferably want to employ doses on the order of $1 \times 10^5$ to $5 \times 10^8$ units/dose, or more preferably on the order of $10^7$ to $10^8$ units/dose. Generally, it will be desirable to administer a sufficient dose of papaverine, or one of its congeners, to provide a serum or plasma concentration of at least about 1 to about 10 uM. For such uses, one will typically desire to administer at least about 150 mg upwards to about 1 gram of papaverine per dose administration, when administered orally. Of course, it will be appreciated by those of skill in the art that lower doses will be required in order to achieve these blood levels by the preferred intravenous route.

In general, upper doses will be limited by the degree of untoward effects exhibited by the drug in the individual patient. The most common, and generally dose-limiting, side effects of interferon therapy are constitutional symptoms, including fever, chills, fatigue, myalgias, headaches and the like. In some instances, granulocytopenia as well as hepatic transaminase elevations have been found to be dose limiting. Accordingly, upper dose limits are most preferably determined in relation to relevant circumstances such as the degree of discomfort experienced by the patient, taking into consideration the severity of the particular case and the response shown by the patient at lower doses. Thus, in some patients and/or in certain severe cases, it may be determined that larger or smaller doses than the foregoing general ranges are appropriate.

As will be appreciated, the present invention is also directed to pharmaceutical compositions formulated to include one or more of the interferons in combination with one or more of the papaverine family agents discussed above. Preferably, in the case of interferon, one will want to employ interferon from either natural or recombinant sources such as those described in EPO Patent Application No. 77,670, incorporated herein by reference. However, while recombinant interferons are preferred, there is no reason why naturally derived compounds cannot be employed with equal efficacy.

In terms of the composition itself, one will typically desire to employ a pharmaceutically acceptable diluent or excipient for parenteral administration. Thus, in that the interferons are typically not orally active, it will be generally desired to prepare the formulations in a manner which will allow their parenteral administration. Suitable carrier vehicles and their formulations are well known in the art and are described, for example, in *Remington's Pharmaceutical Sciences*, 16th Ed., 1980, Mack Publishing Company, edited by Oslo, et al., or as discussed in Goodman, et al., *THE PHARMALOGICAL BASIS OF THERAPEUTICS*, 7th Ed., 1985, both of the foregoing being incorporated herein by reference. Suitable carriers include sterile aqueous solutions including stabilizing agents, e.g., buffers and other protein and pH-stablizing agents, salts and the like. Typically, sterile aqueous interferon compositions will include a dose concentration of between about 0.2 and about 2.0 mg/ml, and about 150 to about 300 mg/dose with respect to papaverine (or a corresponding amount of a congener), in order to allow for the administration of convenient amounts to the patient to be treated.

Interferon compositions of the present invention are typically provided in the form of a sterile lyophilized powder having included therein appropriate salts, etc., to which sterile water may be added to render a final desired concentration, depending on the dose and route which will be employed.

In general, it has been found that the tolerated dose of interferon, and in particular, interferon gamma, as somewhat dependent on the route of administration. Thus, for example, in the case of interferon gamma, the maximum tolerated dose or daily i.m. injection in many patients will generally be on the order of about 0.25 to about 0.5 mg/m$^2$/day or higher, while the maximum tolerated dose for daily 24-hour intravenous infusion is about 0.01 to about 0.025 mg/m$^2$/day. The preferred daily doses of papaverine will be on the order of about 300 mg/day up to a maximum tolerated daily dose of about 1 to 2 grams, administered in 3 or 4 equal daily doses, depending on the particular circumstances. For example, larger single doses may be administered for bolus i.b. administration.

DETAILED DESCRIPTION OF THE PREFERRED EMBODIMENTS

A. Human Interferons

Figure 1:
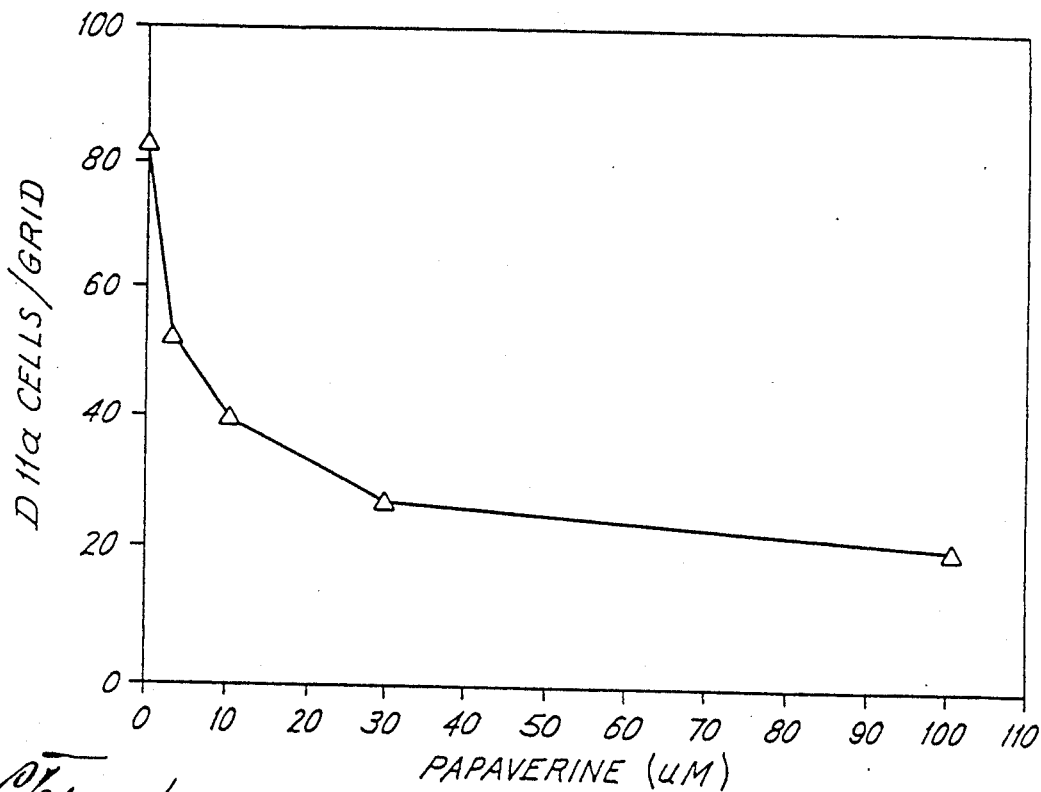
FIG. 1.—The dose-response effect of papaverine on the replication of D11a cells, a malignant mouse cell line, commonly used in the art to exemplify antiproliferative activities.

Human interferons can be classified in three groups on the basis of different antigenicity, biological and biochemical properties.

The first group comprises a family of leukocyte interferons (alpha-interferon, LeIF or IFN-alpha), which are normally produced mainly by constituent cells of human blood upon viral induction. These had been microbially produced and found to be biologically active (Goeddel, et al. (1980), *Nature,* 287:411; Goeddel (1981), *Nature,* 290:20; and Yelverton, et al. (1981), *Nucl. Acids. Ref.,* 9:731). Their biological properties have prompted their use in the clinic as therapeutic agents for the treatment of viral infections and malignant conditions (see, e.g., Gutterman, et al., (1980), *Annals. of Int. Med.,* 93:399).

In the second group is human fibroblast interferon (beta-interferon, FIF or IFN-beta), normally produced by fibroblasts upon viral induction, which has likewise been microbially produced and found to exhibit a wide range of biological activities (Goeddel, et al. (1980), *Nucl. Acids. Ref.,* 8:4057). Clinical trials also indicate its potential therapeutic value. The leukocyte and fibroblast interferons exhibit very clear similarities in their biological properties despite the fact that the degree of homology at the amino acid level is relatively low. In addition, both groups of interferons contained from 165 to 166 amino acids and are typically acid-stable proteins.

Human immune interferon (gamma-interferon, IIF or IFN-gamma), is, in contrast to the alpha- and beta-interferons, pH 2 labile, produced mainly upon mitogenic induction of lymphocytes, and also clearly antigenically distinct from alpha and beta IFN's. Until recently, human immune interferon could only be detected in very minor levels, which evidently hampered its characterization. Human immune interferon was reported to have been partially purified by Yip, et al. (1981), *Proc. Natl. Acad. Sci. USA,* 78:1601, from natural sources More recently, the gene encoding human gamma interferon has been cloned and expressed, resulting in its ready availability to those in the art. A full description of cloning of the human gamma interferon gene, and the subsequent preparation of recombinant IFN-gamma suitable for use herein, is given is EPO Patent Application Publication 0077670.

IFN gamma is a T-cell-derived lymphokine which has been shown to function as a differentiation factor, an immune regulator with macrophage activator effects and as an antimicrobial agent against intracellular protozoa and bacteria (see, e.g., Kurzrock, et al., (1985), *Cancer Res.,* 45:2866–2872). This spectrum of activity of IFN-gamma has led to a therapeutic role for this material in patients with cancer, viral diseases and opportunistic infections. Prior to availability of the above-referenced recombinant sources, reported clinical studies employing IFN-gamma preparations were limited to preliminary pharmacokinetic evaluation of native IFN-gamma, which was available in only limited amounts and of limited purity (see, e.g., Gutterman, et al., (1984), *Cancer Res.,* 44:4164). However, the availability of recombinant IFN-gamma has allowed for the first time, clinical evaluation of purified IFN gamma compositions.

To date, clinical trials of IFN-gamma have involved primarily phase I trials of IFN-gamma pharmacokinetics and toxicity pharmacology in cancer patients (see, e.g., Kurzock, et al. (1985), *Cancer Immunol. Immunother.,* 20:193; Kurzock, et al. (1986), *Jrnl. Clin. Oncol.,* 4:1101; and Vadhan-Raj, et al. (1986) *Jrnl. Clin. Oncol.,* 4:137). These and other studies provide fairly extensive pharmacologic data using highly purified recombinant IFN-gamma, including pertinent pharmacokinetic, toxicologic and scheduling information.

B. Papaverine Family Agents

With respect to pharmacological properties, papaverine is the classical example of a non-specific smooth muscle relaxant (i.e., an antispasmodic). Papaverine can relax all smooth muscle structures, irrespective of type of endogenous or exogenous factors which affect muscular tone. Papaverine is traditionally known as an inhibitor of a cyclic nucleotide phosphodiesterase found in many tissues and can increase the concentration of cyclic adenasine 3', 5'-monophosphate (cyclic AMP).

However, it has been discovered by one of the present inventors that cyclic nucleotide modulation is likely not the prime mechanism through which the papaverine family agents exert their antiviral, and likely their antiproliferative activity as well. This newly discovered mechanism proceeds through inhibition of intracellular calcium flux. That is, the papaverine agents tend to block the release of calcium from intracellular calcium stores. This effect on intracellular-free calcium levels is likely the principal mechanism behind its actions, as opposed to cyclic nucleotide effects.

Therapeutically, papaverine and its congeners, have been employed to lower peripheral resistance, and thereby effect a lowered blood pressure. This, of course, is based on its relaxation activity on smooth muscles of the larger blood vessels and also on its effects on arterioles. Moreover, large doses of papaverine have been shown to prevent various cardiac arrhythmias, but they can also tend to depress A-V as well as intraventricular conduction. Papaverine also increases cerebral blood flow and decreases cerebral vascular resistance. These effects may explain the benefit reported for the use of this drug in cerebral vascular encephalopathy.

As discussed in some detail in co-pending serial no. 07/944,301, the papaverine family agents which have the greatest antiviral activity are those which bear an intact isoquinoline ring structure, wherein the isoquinoline ring nitrogen has an electron available for covalent bond formation. When hydrogen occupies this site (e.g., in the case of tetrohydropapaverine), then the inhibitory activity is reduced dramatically at equimolar doses. When a methyl group occupies this site (e.g., in the case of laudanosine), its antiviral activity is lost almost entirely. The results with salsolidine in glaucine add further support to this view. Based on the present inventors' experimentation and observations, it is proposed that the same holds true in the case of the antiproliferative activity of papaverine. Thus, it will be appreciated that those papaverine family agents not found to have appreciable antiproliferative activity will be those that do not have a true isoquinoline ring, in that the aromaticity of the ring is lost upon addition of substituents to the ring nitrogen. Thus, agents such as ethaverine and dioxyline, which do have a true isoquinoline ring structure, will prove useful in the antiproliferative compositions hereof. Therefore, the present invention is concerned in particular with papaverine family agents having the aromatic isoquinoline ring.

C. Pharmaceutical Compositions

Interferon alpha, beta, gamma, or mixtures of the foregoing, in accordance with the present invention, is typically admixed with a pharmaceutically acceptable diluent, such as a sterile aqueous solution, to give a final concentration of about 0.2 to about 2.0 mg/ml with respect to IFN alpha, beta, gamma, or alpha/beta. With respect to the papaverine family agents, one will want to include a sufficient amount of the agent which will correspond biologically to about 1 to about 10 uM papaverine. A preferable composition will contain about 1.0 mg/ml with respect to interferon and about 300 mg/dose with respect to the papaverine family agent. Such formulation will typically include buffers such as phosphate buffered saline (PBS), or additional additives such as pharmaceutical excipients, stabilizing agents such as BSA or HSA, or salt such as sodium chloride. For parenteral administration, it is generally desirable to further render such compositions pharmaceutically acceptable by insuring their sterility and nonimmunogenicity. Such techniques are generally well known in the art as exemplified by the aforementioned *Remington's Pharmaceuticals*, supra.

It will be appreciated that endotoxin contamination should be kept minimally at a safe level, for example, less than 0.5 ng/mg protein. Moreover, for human administration, preparations should meet sterility, pyrogenicity, general safety, and purity standards as required by the FDA Office of Biologics Standard. Most conveniently, interferon/papaverine compositions are obtained as a sterile lyophilized powder in vials of desired amounts, for storage at 2° to 8° C. and reconstituted by the addition of a desired amount of sterile water immediately before use.

D. Dosages and Administration

Minimum effective interferon and papaverine levels for inhibiting the growth of proliferating cells in accordance with the present invention is determined herein generally by reference to accepted in vitro assays for proliferation inhibition, including assays for determining dose-response inhibition of cell growth and proliferation. By comparing the amount of these agents that is required to achieve an effect commensurate with that of proven therapy, such as interferon therapy, an appropriate plasma drug concentration may be more accurately ascertained. A particular assay preferred by the present inventors to demonstrate the effectiveness of the present compositions in the treatment of proliferative disorders, is through the use of the mouse D11a tumor cell system discussed briefly above. This system provides the advantages of time, reproducibility and quantification of the antiproliferative activity In that this system is accepted in the art, it is believed to be one of the better predictors of activity in man short of clinical trial.

In assays as disclosed more completely in the examples below, it is believed that concentrations, for example, interferon at concentrations as low as about $10^7$ units, in combination with papaverine doses as low as about 150 to 300 mg will provide a synergistic antiproliferative effect in accordance with the present invention. When dosages are given i.m., it will generally be desirable to administer daily doses of about $10^5$ to about $5 \times 10^8$ of interferon, preferably on the order of about $10^7$ to about $10^8$, together with daily doses of the papaverine family agent of about 1 to about 3 grams, preferably on the order of about 1 to about 2 grams/day, depending on the appearance of untoward effects such as fever, chills, nausea, etc. This dose, when administered in one or more daily administrations, will generally achieve a plasma level sufficient to achieve benefits in accordance with the present invention It will generally be desirable to administer additional dosages until an adequate response is observed.

For certain uses in accordance with the present invention, the i.m. route is generally more preferred. This is due to the more consistent plasma levels generally obtainable by this route, as well as the generally longer plasma half life observed. However, to achieve exceedingly high plasma levels, it will generally be desirable to employ a bolus intravenous dose of on the order of about $10^7$ to $10^8$ with respect to interferon and a sufficient amount of the papaverine agent to achieve a serum concentration of between about 1 and about 10 uM.

In the examples which follow, the present invention is exemplified in terms of antiproliferative activity against an accepted tumor cell model, the D11a mouse epidermal tumor cell line. This cell line, described in more detail in Coburn et al. (1979), *Neoplastic Transformation in Differentiated Epithelial Cell Systems In Vitro*, eds. Franks and Wigley, Academic Press, N.Y., pp 113–134; Coburn et al. (1978), *Carcinogenesis, Vol II: Mechanism of Tumor Promotion and Carcinogenesis*, eds. Slaga, Sivak and Boutwell, Raven Press, N.Y., pp 257–271; both of the foregoing being incorporated by reference, is generally accepted as exemplifying a broad spectrum of activity against a wide variety of tumors. Therefore, activity in the case of D11a is believed to translate well into a relatively broad spectrum antitumor agent.

The fact that the present invention is exemplified in terms of in vitro activity is not believed to detract from the validity of the invention. For example, the agents employed herein do not undergo appreciable enterohepatic metabolism prior to distribution throughout the body, nor do they require metabolism for "activation". Likewise, the test cell line employed, D11a, as discussed above, is well accepted as predictive in vitro activity in vivo. For many years, it has been shown that in vitro antitumor activity typically correlates well with in vivo activity. In contrast, the main problem associated with the predictive value of in vitro tests has been the later finding of untoward reactions (toxicities) in vivo that were not seen in vitro. However, in the present instance, these agents, including the interferons as well as the papaverine family agents, have been in clinical use and it is known that untoward reactions will not present a problem. Therefore, it is expected that the present agents can be administered to an infected patient by all routes presently indicated for their use. Moreover, it is further expected that topical preparations will be active in treating hyperplastic and neoplastic lesions of this sort.

EXAMPLE I

The Use of Papaverine Alone or in Combination with Interferon to Inhibit Tumor Cell Growth.

D11a cells, mouse epidermal tumor cell, were obtained from Nancy Coburn, National Cancer Institute. Cells were placed in 35 mm tissue culture dishes in relatively small numbers (approximately 4,000 cells/dish) and the rate of cell replication was measured over a 72 hour period. The drugs (papaverine, interferons) were added to the cell culture at 24 hours and at 24 hour intervals thereafter. The cells were fixed with methanol and stained with 1% crystal violet. The viable cells were then counted using an ocular grid and a grid imprinted on the culture dishes. The mean number of cells surviving was determined for 10 random squares on the grid.

Referring now to FIG. 1 is shown the dose-response effect of papaverine alone on the replication of D11a cells. As will be appreciated from the data displayed therein, as the concentration of papaverine was increased, the number of D11a cells surviving decreased dramatically. An ED50 of approximately 2 to 10 uM was observed. Moreover, the relationship between the number of cells surviving and the concentration of papaverine was nearly linear. Although papaverine did not appear to kill the cells, it exerted a profound cytostatic effect. However, even at the highest concentration employed (100 uM), the number of cells did not decease. Thus, as a antiproliferative agent alone, papaverine is cytostatic rather than cytocidal.

Figure 2:
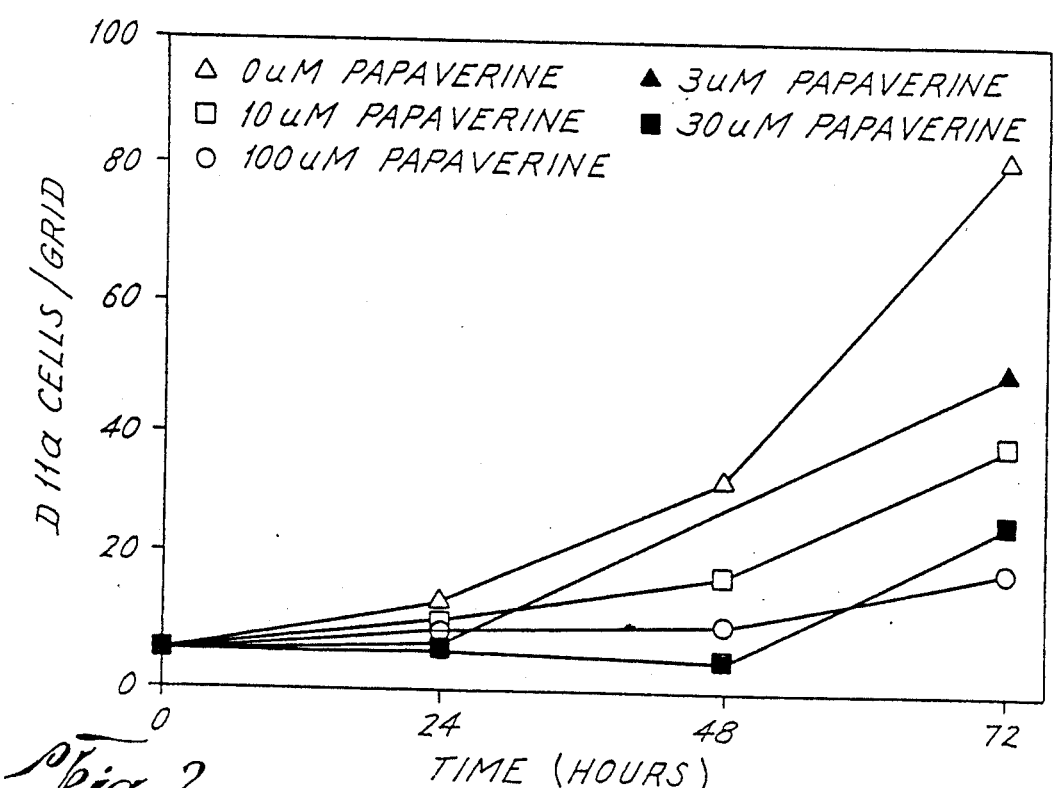
FIG. 2.—The replication of D11a cells in the presence of papaverine.

Referring now to FIG. 2 is shown the replication of the 11a cells in the presence of papaverine alone. In this study, D11a cells were grown in increasing concentration of papaverine, ranging from 0 uM papaverine up to a high dose of 100 uM papaverine. The cells were incubated for a total of 72 hours, with readings being taken at 24, 48 and 72 hours. As well be appreciated, while the cells did continue to grow a small amount in the papaverine, there was a noticeable effect on cell growth, with growths being effective in a more or less does-dependent fashion.

In contrast, when papaverine was employed in combination with interferons, a much more profound effect was observed. Referring to Table 1 below, is shown the effect of papaverine alone, the various interferons alone, as well as combinations of these two in the inhibition of D11a cell growth (disclosed in terms of D11a cells/grid, at 72 hours with a mean of at least 10 grids counted). As will be appreciated, in the case of papaverine alone, about 52 cells/grid observed at the lowest papaverine level (3 uM) ranging to a low of 20 cells/grid at the high end of 100 uM of papaverine. Similarly, in the case of interferon alpha/beta (containing 500 international units per ml of alpha/beta), a cell count of about 61 cells/grid was obtained after 72 hours of incubation. In the case of gamma interferon (at about 50 international units/ml) a more profound effect was observed with only about 37 cells/grid on the average being counted. The most profound effect in the case of interferons alone was when all three were employed i.e., alpha/beta plus gamma wherein the reduction to 18 cells/grid was observed.

effect is dependent on the papaverine concentration. While papaverine does not appear to actually kill the cells, it does stop them from dividing and therefore appears to be an effective antitumor cytostatic agent. Secondly, it was observed from these studies that interferons themselves inhibit the replication of cancer cells much in the same fashion as papaverine. Lastly, and most importantly to the present invention, the studies show quite clearly that papaverine and interferons act together in a synergistic fashion and are much more effective than either of the foregoing agents alone.

The instant invention has been disclosed in connection with standard laboratory procedures used by the applicants. However, it will be apparent to those skilled in the art that variations may be undertaken without departing from the spirit and scope of the invention. More specifically, it will be apparent that certain agents that are both chemically and pharmacologically related may be substituted to achieve the observed antiproliferative effect. For example, new papaverine family agents having in tact isoquinoline ring structures may be developed which exhibit a greater antiproliferative activity than those disclosed herein. However, it will be clear that the present invention is intended to include such improved papaverine family agents, so long as they work synergistically together with interferons as disclosed herein. Additionally, although the present invention is disclosed in terms of activity against D11a mouse epidermal tumor cells, it is contemplated that the agents will be effective in treating a wide variety of tumors. These and similar substitutes will be apparent to those skilled in the art and are within the spirit and scope of the invention.

What is claimed is:

1. A method for inhibiting the growth of neoplastic cells comprising subjecting the cells to an effective concentration of a papaverine family agent in combination with an interferon.

2. The method of claim 1 wherein the papaverine family agent comprises papaverine, ethaverine or dioxyline.

3. The method of claim 1 wherein the interferon comprises interferon gamma.

TABLE 1

| | | Papaverine Inhibition of Cancer Cells | | | | | | | | |
|---|---|---|---|---|---|---|---|---|---|---|
| | | | | | Treatment | | | | | |
| | | Papaverine (μM) | | | Interferon | | | Combination | | |
| | None | 3 | 10 | 30 | 100 | α/β[1] | γ[2] | α/β[1] + γ[2] | α/β[1] + P[3] | γ[2] + P[3] | α/β[1] + γ[2] + P[3] |
| Dila cells/grids[4] | 83 | 52 | 40 | 27 | 20 | 61 | 37 | 18 | 17 | 9 | 24 |

[1]500 international units/milliliter.
[2]50 international units/milliliter.
[3]Papaverine. 100 μM.
[4]Number of cells at 72 h: Mean of at least 10 grids.

The synergism between interferons and papaverine is shown most explicitly in the final column of Table 1 wherein it is shown that the addition of 100 uM of papaverine to alpha/beta resulted in a reduction from 61 cells/grid down to 17 cells/grid. Moreover, in the case of gamma interferon plus papaverine, a reduction from 37 cells/grid to 9 cells/grid was observed. Curiously, the combination of alpha/beta plus gamma plus papaverine, was not quite so active, although the reason for this is a bit unclear.

In general, the conclusions which can be drawn from the foregoing studies are that papaverine inhibits the replication of cancer cells in and of itself and that this 4. The method of claim 1 wherein the interferon comprises interferon alpha.

5. The method of claim 1 wherein the interferon comprises interferon beta.

6. The method of claim 1 wherein the papaverine family agent comprises papaverine and the interferon comprises interferon gamma.

7. The method of claim 1 wherein the neoplastic cells comprise sarcomas, carcinomas or leukemic cells.

8. A pharmaceutical composition comprising a papaverine family agent in combination with an interferon.

9. The composition of claim 8 wherein the papaverine family agent comprises papaverine, ethaverine or dioxyline.

10. The composition of claim 8 wherein the interferon comprises interferon gamma.

11. The composition of claim 8 wherein the interferon comprises interferon alpha.

12. The composition of claim 8 wherein the interferon comprises interferon beta.

13. The composition of claim 8 wherein the papaverine family agent comprises papaverine and the interferon comprises interferon gamma.

14. The pharmaceutical composition of claim 8 wherein the papaverine family agent and interferon are admixed in a preparation suitable for topical administration.

* * * * *